United States Patent [19]

Poli et al.

[11] Patent Number: 5,767,112
[45] Date of Patent: Jun. 16, 1998

US005767112A

[54] MUSCLE RELAXANT PHARMACEUTICAL COMPOSITIONS

[75] Inventors: Stefano Poli; Tiziano Crimella, both of Milan; Ambrogio Magni. Osnago-Como; Luigi Moro. Cairate-Varese, all of Italy

[73] Assignee: Poli Industria Chimica, S.p.A., Milan, Italy

[21] Appl. No.: 586,088

[22] Filed: Jan. 16, 1996

Related U.S. Application Data

[63] Continuation-in-part of Ser. No. 390,488, Feb. 17, 1995, abandoned.

[30] Foreign Application Priority Data

Oct. 21, 1994 [IT] Italy ..................... MI94A2166

[51] Int. Cl.$^6$ .......................... A61K 31/58; A61K 9/127
[52] U.S. Cl. .............................. 514/172; 424/450
[58] Field of Search ...................... 514/172; 424/450

[56] References Cited

U.S. PATENT DOCUMENTS

| | | |
|---|---|---|
| 3,553,212 | 1/1971 | Hewett et al. . |
| 3,872,091 | 3/1975 | Hewett et al. . |
| 4,110,326 | 8/1978 | Tuba et al. . |
| 4,237,126 | 12/1980 | Carlyle et al. . |
| 4,297,351 | 10/1981 | Carlyle et al. . |
| 5,418,223 | 5/1995 | Palepu et al. ................ 514/23 |
| 5,469,854 | 11/1995 | Unger et al. ............. 128/662.02 |
| 5,472,706 | 12/1995 | Friedman et al. ............ 424/450 |

FOREIGN PATENT DOCUMENTS

| | | |
|---|---|---|
| 0 008 824 | 8/1979 | European Pat. Off. . |
| 94/17808 | 8/1994 | WIPO . |

OTHER PUBLICATIONS

Reminton's Pharmaceutical Sciences, 16th ed. pp. 1483–1484 1980.

W.R. Buckett et al; Pancuronium Bromide and Other Steroidal Neuromuscular Blocking Agents Containing Acetylcholine Fragments; *Journal of Medicinal Chemistry* 16 No. 10; pp. 1116–1124 (1973).

*Primary Examiner*—Raymond Henley
*Attorney, Agent, or Firm*—Townsend and Townsend and Crew LLP; Lori Ann Morgan

[57] ABSTRACT

The invention relates to pharmaceutical compositions for parenteral administration. The compositions comprise an amount of neuromuscular blocking agent effective to produce muscular relaxation, and at least one zwitterionic substance having an isoionic point not greater than 7. The zwitterionic substance is present in an amount of between about 2 and about 30 percent by weight, based on the weight of the composition. The resulting composition has a pH of less than 7.

14 Claims, No Drawings

MUSCLE RELAXANT PHARMACEUTICAL COMPOSITIONS

RELATED APPLICATIONS

The instant application is a continuation-in-part application of U.S. patent application Ser. No. 08/390,488, filed 17 Feb. 1995 now abandoned, the disclosure of which is incorporated herein by reference in its entirety.

FIELD OF THE INVENTION

The present invention relates to pharmaceutical compositions, and particularly to muscle relaxant pharmaceutical compositions.

BACKGROUND OF THE INVENTION

Neuromuscular blocking agents are employed in therapy as coadjuvants in surgical anaesthesia to obtain relaxation of skeletal muscles. Typically, therapy is performed by i.v. administration of a suitable dosage form. This dosage form may be administered by dissolving a freeze-dried powder, containing the active ingredient associated with some excipients, in water or another suitable solvent.

One neuromuscular blocking agent, vecuronium bromide, was first described in U.S. Pat. No. 3,553,212 to Hewett et al. Various formulations for neuromuscular blocking agents, including vecuronium bromide, have also been proposed. One of such formulations is described in U.S. Pat. Nos. 4,237,126 and 4,297,351 to Carlyle et al. and European Patent No. 008,824, and includes the acid addition salts of a monoquaternized compound in position 16 of the 2,16-dipiperidine androstane nucleus. The acid addition salts which are proposed therein include the hydrochloride, bromohydrate, maleate, nitrate, and phosphate salts. This formulation, specifically the acid addition salt of vecuronium bromide, is currently being marketed by Akzo Chemical under the tradename NORCURON®.

A second formulation of neuromuscular blocking agents is proposed in PCT Publication No. WO 94/17808 to Inpharm. The proposed formulation is obtained by dissolving vecuronium bromide or an analogue thereof in water saturated with carbon dioxide, or in an organic solvent, filling the solution into containers, removing the solvent by lyophilization, and hermetically closing the container. Thereafter the lyophilizate may be reconstituted to provide a solution having a pH suitable for injection, i.e., a pH of between 7 and 7.4. The lyophilizate may be reconstituted with an amino acid solution of sufficient concentration to obtain a pH in the desired range.

It is well known that a solution of the active ingredient, i.e., the neuromuscular blocking agent in water produces a basic reaction. Accordingly, the stability of a solution of neuromuscular blocking agent depends upon the pH of the solution. Preparations of neuromuscular blocking agents must be stable for at least a few hours between preparation and administration. There remains a need in the art for stable solutions of neuromuscular blocking agents, which are suitable for parenteral administration. There further remains a need in the art for neuromuscular blocking agent formulations which avoid the use of acid addition salts of the active agent.

SUMMARY OF THE INVENTION

As a first aspect, the present invention relates to pharmaceutical compositions for parenteral administration. The compositions of the invention comprise an amount of neuromuscular blocking agent effective to produce muscular relaxation, and at least one zwitterionic substance having an isoionic point not greater than 7. The zwitterionic substance is present in an amount of between about 2 and about 30 percent by weight, based on the weight of the composition. The resulting composition has a pH of less than 7.

As a second aspect, the present invention relates to a method of preparing a pharmaceutical composition containing a neuromuscular blocking agent. The method comprises (a) solubilizing an amount of neuromuscular blocking agent sufficient to produce muscular relaxation, and between about 2 and about 30 percent by weight, based on the weight of the composition, of a zwitterionic substance having an isoionic point of not less than 7, in water to produce a solution; and (b) lyophilizing the solution to produce a lyophilizate. Thereafter, the lyophilizate may be hermetically sealed in a suitable container for reconstitution.

The foregoing and other aspects of the present invention are explained in detail in the detailed description of the invention set forth below.

DETAILED DESCRIPTION OF THE INVENTION

As used herein, the term "zwitterionic agent" has its conventional meaning in the art. In particular, zwitterionic agents are those agents which exist in a zwitterion state at a pH equivalent to the isoelectric point such that the net charge on a molecule in solution is zero, and the positive and negative groups are mutually ionized. The terms "lyophilize", "lyophilized", and "lyophilizing", and derivatives thereof, all have their conventional meaning in the art. Specifically, these terms refer to the process of freeze-drying. The term "lyophilizate" refers to the product of the freeze-drying process.

The neuromuscular blocking agents which may advantageously be employed in the instant invention include those conventional neuromuscular blocking agents known in the art. For example, suitable neuromuscular blocking agents include, but are not limited to vecuronium bromide, pancuronium bromide, pipecuronium bromide, rocuronium bromide, and the like. The neuromuscular blocking agent is included in a therapeutically effective amount, i.e., an amount sufficient to produce skeletal muscle relaxation. Typically, the neuromuscular blocking agent is present in an amount of between about 0.01 and about 2.5 percent by weight based upon the weight of the solution, and preferably between about 0.1 and about 1 percent by weight.

According to the methods of the present invention, the formulation is prepared by solubilizing the neuromuscular blocking agent, in combination with a zwitterionic substance, in water to produce a solution. Thereafter the solution is subjected to lyophilization to produce a lyophilizate. Any conventionally known zwitterionic substance may be employed in the methods of the present invention. Typically, suitable zwitterionic substances will have an isoionic point of less than 7. Examples of suitable zwitterionic substances include amino acids and phospholipids. Preferably, the zwitterionic substance is selected from amino acids having an isoionic point of less than 7. Examples of amino acids which are useful in the methods of the present invention include but are not limited to glycine, serine, methionine, alanine, isoleucine, leucine, phenylalanine, proline, hydroxyproline, tryptophan, tyrosine, valine, and cystine. Preferably, the zwitterionic substance is selected from glycine and serine.

Amino acids having an isoionic point of less than 7 are incapable of forming acid addition salts with the neuromuscular blocking agent due to the dissociation constants of their ionic groups. For example, it is known that vecuronium bromide has a pKa of 8.97, corresponding to a pKb of 5.03. See, *American Hospital Formulatory Service*, published by Amer. Soc. Hosp. Pharm., ed. 1992, page 736. In table I below, pKa values are listed jointly with corresponding values of their isoionic point for zwitterionic substances which can be used in the present invention.

TABLE I

Zwitterionic Substances

| Zwitterionic Substance | pKa | pI |
|---|---|---|
| alanine | 9.87 | 6.10 |
| glycine | 9.78 | 6.06 |
| hydroxyproline | 9.73 | 5.82 |
| serine | 9.15 | 5.68 |
| leucine | 9.24 | 6.04 |
| methionine | 10.6 | 5.91 |
| proline | 9.87 | 6.30 |
| valine | 9.72 | 6.00 |

See, *Handbook of Chemistry and Physics*, C.R.C. Press 1988–1989 ed. 69, page C107.

The pKa values for the zwitterionic substances above are much greater than the corresponding value for vecuronium bromide. These substances are therefore, stronger bases than vecuronium bromide. Accordingly, if kept at a pH equal to the isoionic point, or at any pH greater than the pKb of vecuronium bromide (i.e., higher than 5.1), these substances are capable of preferentially forming ion pairs with the ions originating from the dissociation of acid groups present in the vecuronium bromide solution.

The zwitterionic substance may also be comprised of a phospholipid. Any conventional phospholipid may be employed in the methods of the present invention. Typically, the phospholipids of the instant invention include a monoprotic phosphoric group and an electron donor group capable of forming an internal salt. The preferred phospholipids for use in the present invention include but are not limited to phosphatidyl cholines, and phosphatidylethanolamines.

These zwitterionic substances are also capable of acting as surfactants or cosurfactants in the formation of stable emulsions and microemulsions. According to this embodiment, an emulsion or microemulsion is formed by solubilizing and emulsifying the neuromuscular blocking agent, the phospholipid, and suitable emulsification agents such as cholesterol in a aqueous dispersion medium to create a dispersed phase containing the neuromuscular blocking agent and zwitterionic substance, and an aqueous continuous phase.

These zwitterionic substances are also capable of forming liposomes in the presence of excess water and in the absence of an oily phase. In this embodiment of the invention, the liposomes entrap and mask the neuromuscular blocking agent and consequently solubilize and stabilize the same. The solutions are prepared by solubilizing the neuromuscular blocking agent and zwitterionic substance in an aqueous dispersion medium to create a dispersed phase containing the liposomes of the neuromuscular blocking agent and zwitterionic substance and an aqueous continuous phase.

It has surprisingly been found that maintaining the pH of the solutions of neuromuscular blocking agent and zwitterionic substance below 7 results in substantially more stable solutions than solutions of the neuromuscular blocking agent at neutral or higher pH. The improved stability resultant from the lower pH solutions is related to the basic nature of the reaction of the neuromuscular blocking agents with water. Typically, the pH of the solutions obtained according to the methods of the present invention is between about 4.5 and about 6.9, preferably between about 5 and about 6. Furthermore, in addition to the desired result of increased stability, the lower pH of the solutions according to the present invention results in preparations which are more physiologically acceptable than conventional formulations. Accordingly, an improved tolerability pattern is achieved by administration of the compositions of the present invention.

The desired pH range for the solutions of the present invention is partly a function of the quantity of zwitterionic substance which is included in the formulation. For example, increasing amounts of zwitterionic substance result in decreasing pH. Generally, the zwitterionic substance is included in the amount of between about 0.01 and about 30 percent by weight of the entire composition, preferably between about 2 and 30 percent by weight, more preferably between about 2 and 20 percent by weight, and even more preferably between about 5 and 10 percent by weight.

If necessary, the pH of the solution containing the neuromuscular blocking agent and the zwitterionic substance may be adjusted to the desired level, i.e. to restore the isoionic pH, by addition of appropriate quantities of dilute inorganic acid. One skilled in the art may readily determine appropriate quantities of dilute inorganic acid to be added to a specific solution of neuromuscular blocking agent and zwitterionic substance, by observing the change in pH during the addition of dilute inorganic acid. Suitable inorganic acids for use in the present invention are well known to those skilled in the art. The preferred inorganic acid is hydrochloric acid.

As will be readily apparent to those skilled in the art, the formulation may optionally include any of a variety of auxiliary substances. Suitable auxiliary substances will not materially affect the fundamental characteristics of the formulation. Examples of auxiliary substances include but are not limited to antioxidants such as sodium metabisulfite, buffering agents such as dilute mineral acid, and cryoprotectants such as mannitol.

Once a solution is prepared, having the desired pH for stability, the solution of neuromuscular blocking agent and zwitterionic substance is lyophilized to produce a lyophilizate. Lyophilization may be accomplished according to any suitable means known to those skilled in the art. For example, the solution may be lyophilized by first placing the desired quantity in a vessel such as an ampoule suitable for reconstitution, and subjecting the solution to freezing at temperatures from about −40° C. to about −50° C. to achieve a residual moisture content of less than about 1 percent. Those skilled in the art may readily determine other suitable methods of carrying out the lyophilization of the solution according to the present invention, accordingly, such methods are contemplated by the instant invention.

Subsequent to lyophilization, the vessel containing the lyophilizate is typically sealed to prevent contamination. Generally, the vessel is sealed in a manner to provide a hermetically sealed vessel for the lyophilizate. Suitable methods of hermetically sealing the vessel are known to those skilled in the art.

Subsequently, the hermetically sealed vessels containing the lyophilizate may be stored until use. At or near the time of use, the lyophilizate may be reconstituted to provide a solution suitable for injection. Typically, the lyophilizate is reconstituted with an appropriate quantity of water suitable for injection. Alternatively, the lyophilizate may be reconstituted with an aqueous solution comprising water and one or more additional agents suitable for injection. Additional agents may include amino acids, parabens, benzylalcohol and other conventionally known injectable excipients.

The following examples are provided to illustrate the present invention, and should not be construed as limiting thereof. In these examples, l means liter(s), ml means milliliter(s), g means gram(s), % means percent by weight, w/v means weight per volume, °C. means degrees Centigrade, and hr means hour(s).

EXAMPLE 1

In 1 l of water suitable for an injection, 1.8 g of methyl p-hydroxybenzoate and 0.2 g of propyl p-hydroxybenzoate are dissolved while heating. After cooling the solution, 105 g of glycine, and 4.2 g of vecuronium bromide are added thereto. The solution is filtered through a sterilizing membrane and divided into 1 ml ampoules which are lyophilized before sealing.

At the time of use, the lyophilizate is reconstituted using water suitable for injection. The prepared product, kept for 24 hr at 4° C. shows a slight decrease in potency, but is sufficiently stable to remain in conformity with activity specifications.

EXAMPLE 2

A 5% w/v glycine solution in water suitable for injection is prepared in a 3 l reactor. Vecuronium bromide is dissolved in this solution up to a 0.4% w/v concentration and, after sterilizing filtration, the solution is brought to pH equal to the isoionic point of glycine (i.e., 6.1). Thereafter, the solution is filled into ampoules to the unitary extractable volume of 2 ml. The ampoules are lyophilized at −40° C. to a residual moisture content of <1%.

Under these conditions the contents of the ampoules are reconstituted with water suitable for injection, and the preparation remains unaltered when preserved at 4° C. The preparation exhibits acceptable levels of degradation products, present in negligible quantities, if kept at room temperature for 24 hr subsequent to reconstitution.

EXAMPLE 3

A 5% w/v serine solution is prepared in a 3 l reactor in water suitable for injection. Vecuronium bromide is dissolved up to a 0.4% w/v concentration in this solution and, before sterilizing filtration, the solution is brought to a pH value equal to the isoionic point of serine (i.e., 5.67) by addition of dilute hydrochloric acid. The resulting solution is divided into ampoules. The ampoules are lyophilized at −40° C. to a residual moisture content of <1%. The content of the ampoules prepared under these conditions and reconstituted with water suitable for injection exhibit an activity decrease of <1% after preservation for 24 hr at 4° C. The preparation exhibits acceptable levels of degradation products, present in negligible quantities, if kept at room temperature for 24 hr subsequent to reconstitution.

EXAMPLE 4

The ampoules are prepared according to Example 3 except that the pH of the solution is brought to 5.2 by addition of a few drops of dilute inorganic acid. The stability profile of the preparation is similar to that obtained in Example 3. After 3 days of preservation at 4° C. of the reconstituted preparation, the preparation does not show appreciable degradation, and the quantity of active ingredient is not appreciably decreased.

EXAMPLE 5

Ampoules are prepared according to Example 3. Thereafter, the contents of the ampoules are reconstituted using a suitable volume of an injectable micronised emulsion containing 20% of soja lipids, 1.2% of phospholipids, and 2.25% of glycerol in water for suitable injection. The emulsion is commercially available under the tradename INTRALIPID®. The stability profile of the preparations is similar to that obtained in Example 3. After 4 days of preservation at 4° C., the potency decrease is not more than 3%.

EXAMPLE 6

Tocopherol acetate (0.2 g), 8 g of soja phosphatidylcholine and 1.5 g of cholesterol are dissolved in 30 g of warm ethyl alcohol. Thereafter 4.2 g of vecuronium bromide is added. Mannitol (50 g) is dissolved separately in 800 ml of water and warmed to 60° C. The two solutions are mixed using a turboemulsifier homogenizer and brought to final volume of 1 l by addition of water suitable for injection.

After filtration through a 0.45 micron membrane, the liposomic suspension is divided into vials and lyophilized by freezing to −45° C. for 5 hr on precooled plates, progressively desiccating to 40° C. to a final pressure value of 0.1 mbar, vacuum breaking with nitrogen, and sealing the vials. A liposomic suspension is prepared with a solution containing 0.1% glycine, 0.5% benzyl alcohol and a suitable amount of hydrochloric acid to adjust the pH to 5.5. The stability profile of the prepared suspension is acceptable for at least 6 hrs.

EXAMPLE 7

In a 3 l reactor, a 10% w/v glycine solution in water suitable for injection is used to dissolve vecuronium bromide to a concentration of 0.4% w/v. The pH is adjusted to 5.2 by addition of dilute inorganic acid, and the solution is filtered through a 0.22 micron sterilizing filter, taking care to receive the filtrate in a sterile room. The solution is partitioned into glass type I vials to the individual volume of 2.5 ml for lyophilization. A parenterally administrable solution can be obtained by reconstituting the freeze-dried powder with water suitable for injection.

The stability of the prepared solutions conforms to the requirements for administration in that in 0.9% benzyl alcohol solution, a potency decrease is not detected for as long as 5 days of storage in refrigerated conditions at 2°–8° C.; and in water for suitable injection the potency is maintained for at least 24 hr at room temperature or refrigerated conditions at 2°–8° C.

EXAMPLE 8

Freeze-dried cakes (lyophilizates) prepared according to the methods of the present invention are extracted with an apolar organic solvent. The results indicate that more than 90% of vecuronium bromide is extracted from the formulation prepared according to the present invention. In contrast, the extraction of a sample of the commercially available vecuronium bromide formulation resulted in only 20% extraction of vecuronium bromide compound. The results indicate that the main component of commercial formulation is the acid addition salt of vecuronium bromide, and further demonstrate that the processes of the present invention do no convert the vecuronium bromide compound to the acid addition salt form.

The foregoing is illustrative of the present invention and is not to be construed as limiting thereof. The invention is That which is claimed is:

1. A pharmaceutical composition for parenteral administration comprising:
   (a) an amount of neuromuscular blocking agent effective to produce muscular relaxation; and
   (b) between about 2 and about 30 percent by weight, based on the weight of the composition, of at least one zwitterionic substance having and isoionic point not greater than 7 and selected from the group consisting of glycine, serine, cysteine, valine, isoleucine, leucine, methionine, proline, hydroxyproline, alanine, phenylalanine, tyrosine, tryptophan, and phospholipid, said composition having a pH of between about 5.2 and about 5.6.

2. (Once Amended) The pharmaceutical composition according to claim 1, wherein said neuromuscular blocking agent is selected from the group consisting of vecuronium bromide, pipecurium bromide, and rocuronium bromide.

3. The pharmaceutical composition according to claim 1, wherein said neuromuscular blocking agent is vecuronium bromide.

4. The pharmaceutical composition according to claim 1, wherein said neuromuscular blocking agent is present in an amount of between about 0.01 and about 2.5 percent by weight based on the weight of the composition.

5. The pharmaceutical composition according to claim 1, wherein said zwitterionic substance is glycine.

6. The pharmaceutical composition according to claim 1, wherein said zwitterionic substance is serine.

7. The pharmaceutical composition according to claim 1, wherein said zwitterionic substance is present in an amount of between about 2 and about 20 percent by weight of the composition.

8. The pharmaceutical composition according to claim 1, wherein said zwitterionic substance is present in an amount of between about 5 and about 10 percent by weight of the composition.

9. The pharmaceutical composition according to claim 1 further comprising one or more auxiliary substances selected from the group consisting of antioxidants, buffering agents, cryoprotectants, and combinations thereof.

10. The pharmaceutical composition according to claim 9, wherein said cryoprotectant is mannitol.

11. The pharmaceutical composition according to claim 9, wherein said buffering agent is dilute mineral acid.

12. The pharmaceutical composition according to claim 1, wherein said zwitterionic substance is a phospholipid.

13. The pharmaceutical composition according to claim 12, further comprising phospholipidic vesicles containing at least one phospholipid and an aqueous dispersion medium.

14. The pharmaceutical composition according to claim 12, further comprising liposomes containing at least one phospholipid and an aqueous dispersion medium.

* * * * *